(12) United States Patent
Schirmer et al.

(10) Patent No.: US 8,052,933 B2
(45) Date of Patent: Nov. 8, 2011

(54) DEVICE AND METHOD FOR ENTRAPPING AN INDIVIDUAL'S BREATH AS A KEEPSAKE

(75) Inventors: Glen Willard Schirmer, Gold Coast (AU); Rodrick Alexander Payne, Kowloon (HK)

(73) Assignee: MSTK Limited, Hong Kong (HK)

( * ) Notice: Subject to any disclaimer, the term of this patent is extended or adjusted under 35 U.S.C. 154(b) by 2070 days.

(21) Appl. No.: 11/053,791

(22) Filed: Feb. 8, 2005

(65) Prior Publication Data

US 2006/0051245 A1    Mar. 9, 2006

Related U.S. Application Data

(60) Provisional application No. 60/606,965, filed on Sep. 3, 2004.

(51) Int. Cl.
*B01L 9/00* (2006.01)

(52) U.S. Cl. ........ 422/102; 422/500; 422/547; 600/543; 600/372; 600/300

(58) Field of Classification Search .................. 422/102, 422/84, 99, 500, 547; 600/543, 372, 300
See application file for complete search history.

(56) References Cited

U.S. PATENT DOCUMENTS

| 5,211,181 A | 5/1993 | Delente |
| 5,245,991 A | 9/1993 | Kawaguchi |
| 5,525,299 A * | 6/1996 | Lowe ............................ 422/99 |
| 5,711,306 A | 1/1998 | Guilluy |
| 6,468,477 B1 | 10/2002 | Hamilton et al. |

FOREIGN PATENT DOCUMENTS

WO    WO 0201182 A1    1/2002

* cited by examiner

*Primary Examiner* — Christine T Mui (74) *Attorney, Agent, or Firm* — Kelly Lowry & Kelley, LLP (57) ABSTRACT

A device for capturing an individual's breath as a keepsake includes a hollow blow-pipe insertable through an aperture through a neck fitted into an aperture of the vessel. After introducing one or more individual's breath into the vessel, the vessel is sealed, such as by using a plug removably attached to an end of the blow-pipe disposed within the vessel and configured to engage the neck as the blow-pipe is removed from the vessel and disengaged from the plug.

22 Claims, 7 Drawing Sheets

DEVICE AND METHOD FOR ENTRAPPING AN INDIVIDUAL'S BREATH AS A KEEPSAKE

RELATED APPLICATION

This application claims priority to U.S. Provisional Application Ser. No. 60/606,965, filed on Sep. 3, 2004.

BACKGROUND OF THE INVENTION

The present invention generally relates to mementos and keepsakes. More particularly, the present invention resides in a method for entrapping an individual's breath for keeping as a memento or keepsake.

There are many well-known and diverse ways to express one's love to another and to memorialize a loved one. For example, on special occasions greeting cards and the like are often exchanged. Love letters, photographs, may also be exchanged and kept for safe-keeping and later reviewed.

When a loved passes on, these mementos and keepsakes can have additional meaning and importance as they are a link to the deceased individual.

In some instances, the deceased individual is cremated and the ashes, or at least a portion thereof, are kept in a decorative vase or the like for display in the relative's or loved one's home. The keeping of the ashes of the deceased loved one brings peace to the surviving relative as the relatives feel they have maintained a presence of the deceased loved one in their home. The urn can also serve as a reminder of the deceased individual.

However, there is a continuous need for a memento or keepsake which actually captures the essence of the individual while he or she is still living. Such a memento or keepsake can become a touching moment at the time that it is given. The present invention fulfills these needs and provides other related advantages.

SUMMARY OF THE INVENTION

The present invention resides in a device used to entrap an individual's breath for keeping as a memento or keepsake.

The device generally comprises a vessel having an aperture formed therein. A hollow blow-pipe is insertable through the vessel aperture for introducing the individual's breath into the vessel. Preferably, the blow pipe includes a mouth piece at an end thereof. The mouthpiece may be removably attached to the blow-pipe.

In one embodiment, the blow-pipe may include multiple inlets, or a blow-pipe adapter having multiple inlets may be attachable to the blow-pipe such that two or more individuals can simultaneously introduce their breath into the vessel.

The vessel is comprised of a material which is adapted to retain air therein for a prolonged period of time. In a particularly preferred embodiment, the vessel comprises a glass bulb having a neck fitted into an aperture thereof. The device may include a base for holding the vessel and displaying a photograph or written material. A cap is insertable into the neck of a vessel, so as to permanently seal the vessel.

Means are provided for sealing the vessel after introducing the one or more individual's breath therein. In a particularly preferred embodiment, the sealing means comprises a plug that is removably attached to an end of the blow-pipe disposed within the vessel. The plug typically includes an air passageway in communication with an end of the hollow blow-pipe. The plug is configured to engage the neck and seal the vessel. Preferably, the neck includes a chamber configured to receive the plug to seal the vessel. A plug is removably attached to the end of the blow-pipe such that the blow-pipe can be removed from the device after it is sealed.

Other features and advantages of the present invention will become apparent from the following more detailed description, taken in conjunction with the accompanying drawings, which illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENTS

As shown in the accompanying drawings, for purposes of illustration, the present invention resides in a device, generally referred to by the reference number 10, for entrapping an individual's breath. The device 10 is intended to be kept or displayed as a memento or keepsake of the individual or the time when the device 10 was given as a gift to another.

Figure 1:
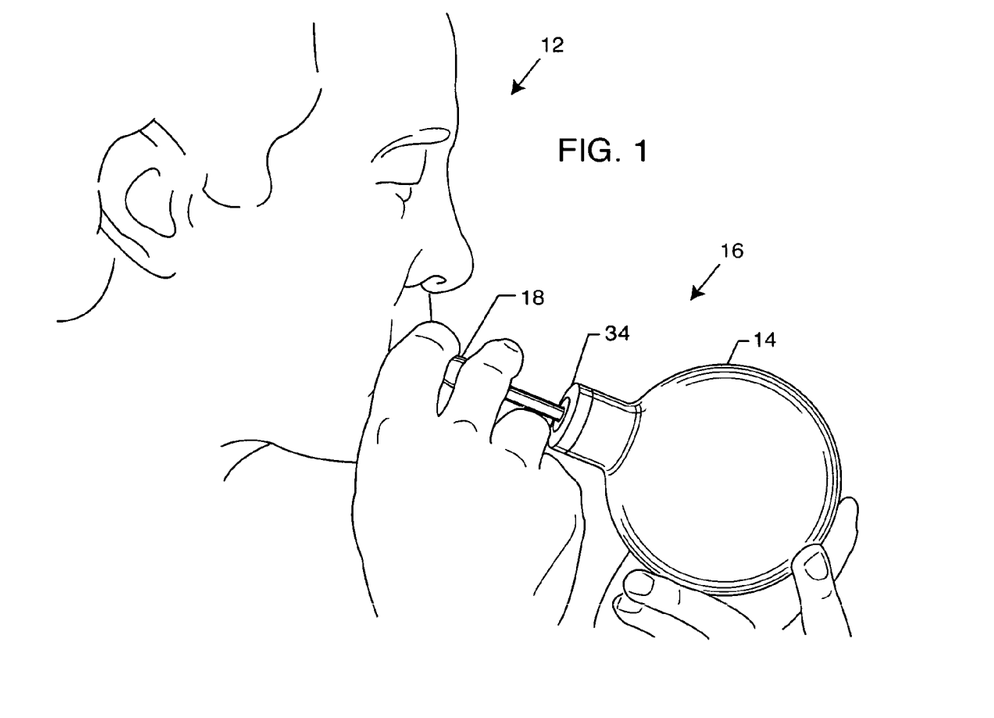
FIG. 1 is a perspective view of an individual blowing into a vessel, in accordance with the present invention.
Figure 2:
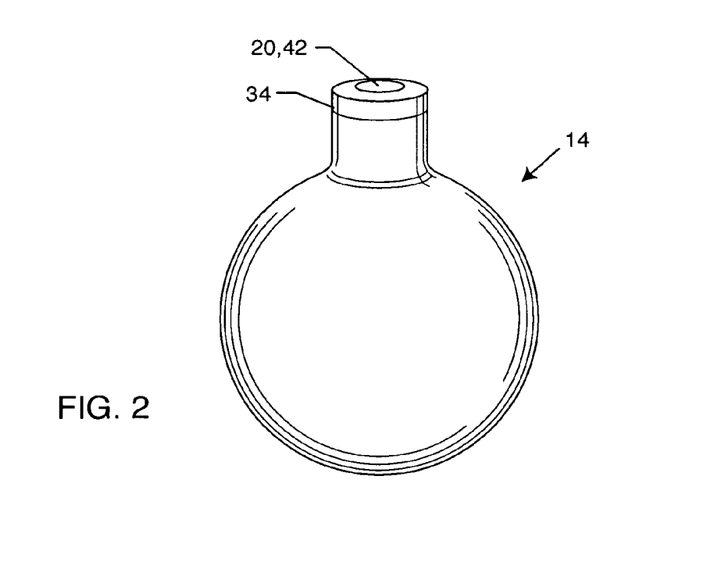
FIG. 2 is a front perspective view of the glass bowl apparatus used in accordance with the present invention.

With reference now to FIG. 1, in accordance with the present invention, an individual 12 blows into the device 10 such that the individual's breath is contained within a vessel 14 of the device 10. The vessel 14 is comprised of a material that is adapted to retain the individual's breath therein for a prolonged period of time. In a particularly preferred embodiment, as illustrated, the vessel 14 comprises a glass bulb. The vessel 14 can be decorated or comprised of a decorative material. It should be understood that the vessel 14 can be any configuration and comprised of many different materials so long as the vessel 14 is capable of entrapping an individual's breath and retaining it over a long period of time.

With reference to FIGS. 1-4, the individual 12 preferably uses a hollow blow-pipe 16, which preferably has a mouthpiece 18 attached at an end thereof for blowing into an aperture 20 of the vessel 14. The mouthpiece 18 may be put at the end of the blow-pipe 16, or removably attached thereto, such as by threaded attachment or the like. After the individual 12 blows into the vessel 14, it is sealed such that the individual's breath cannot escape therefrom so that the sealed vessel 14 can be kept as a memento or keepsake of the individual, and the time and event when this took place.

Figures 3, 4:
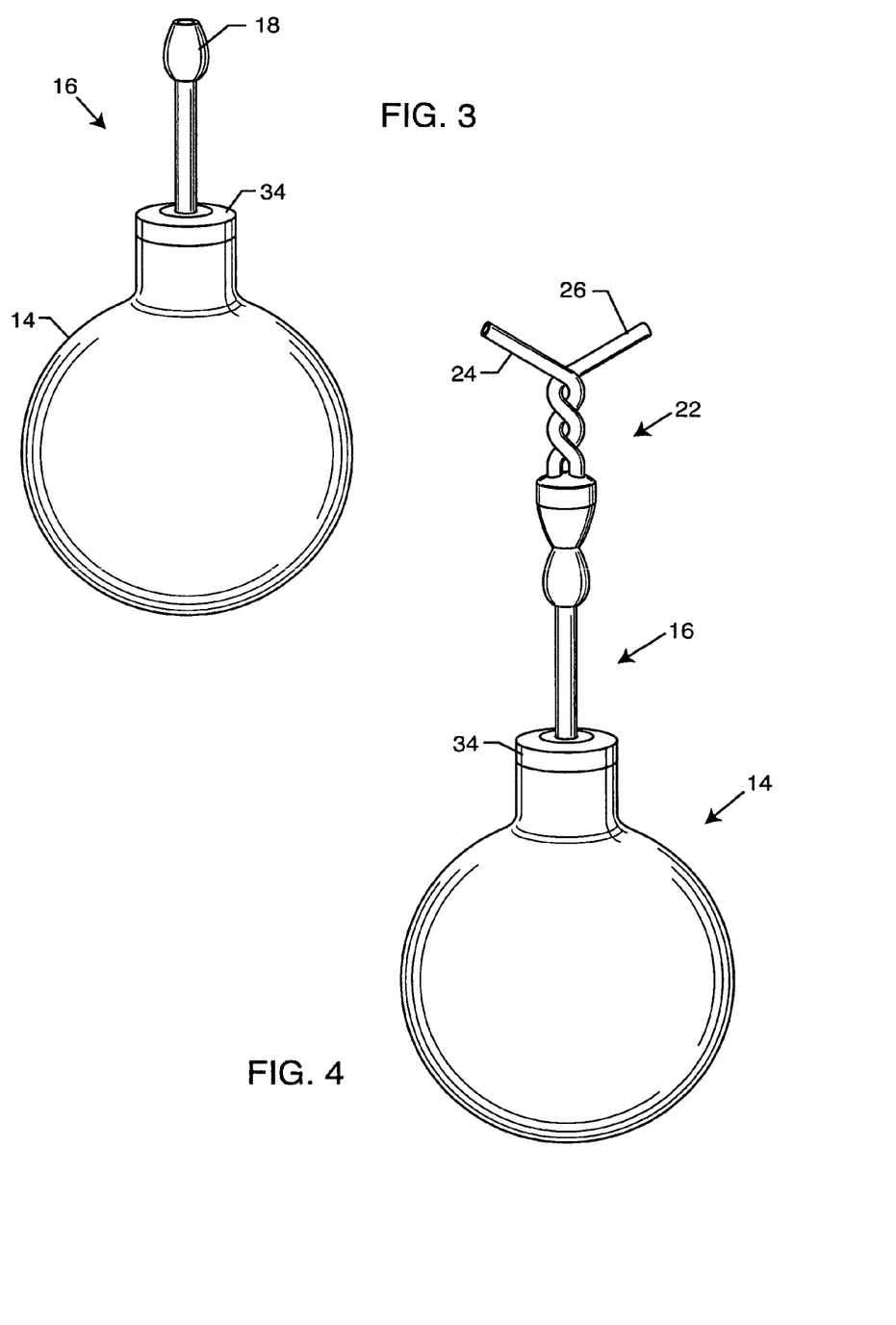
FIG. 3 is a front perspective view of the vessel having a blow-pipe extending therein.
FIG. 4 is a front perspective view of the vessel having a blow-pipe adaptor having multiple inlets attached to the blow-pipe.
Figure 5:
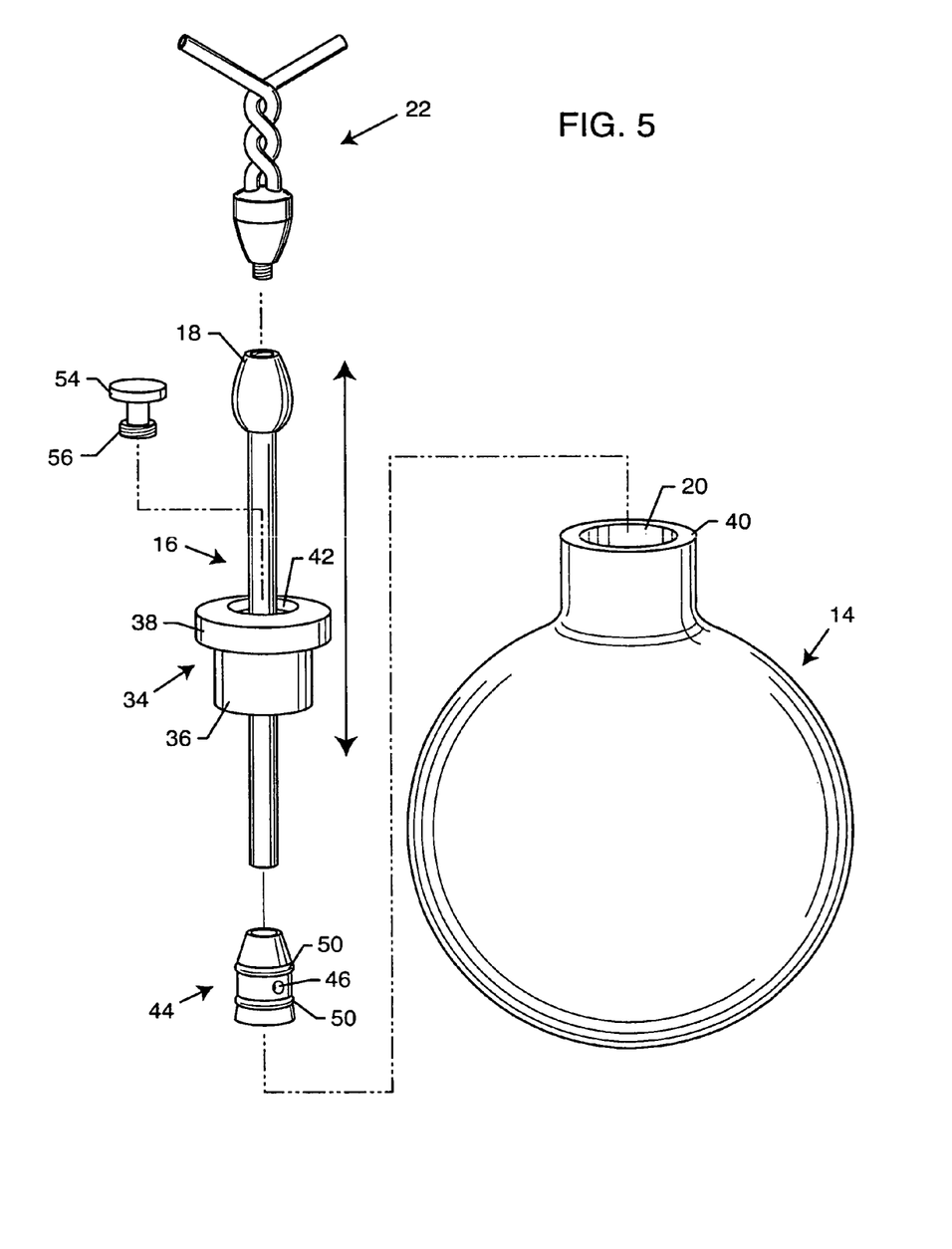
FIG. 5 is an exploded perspective view of the various component parts of the device of FIG. 4, illustrating the slidable relationship of the blow-pipe and a neck of the device.
Figure 6:
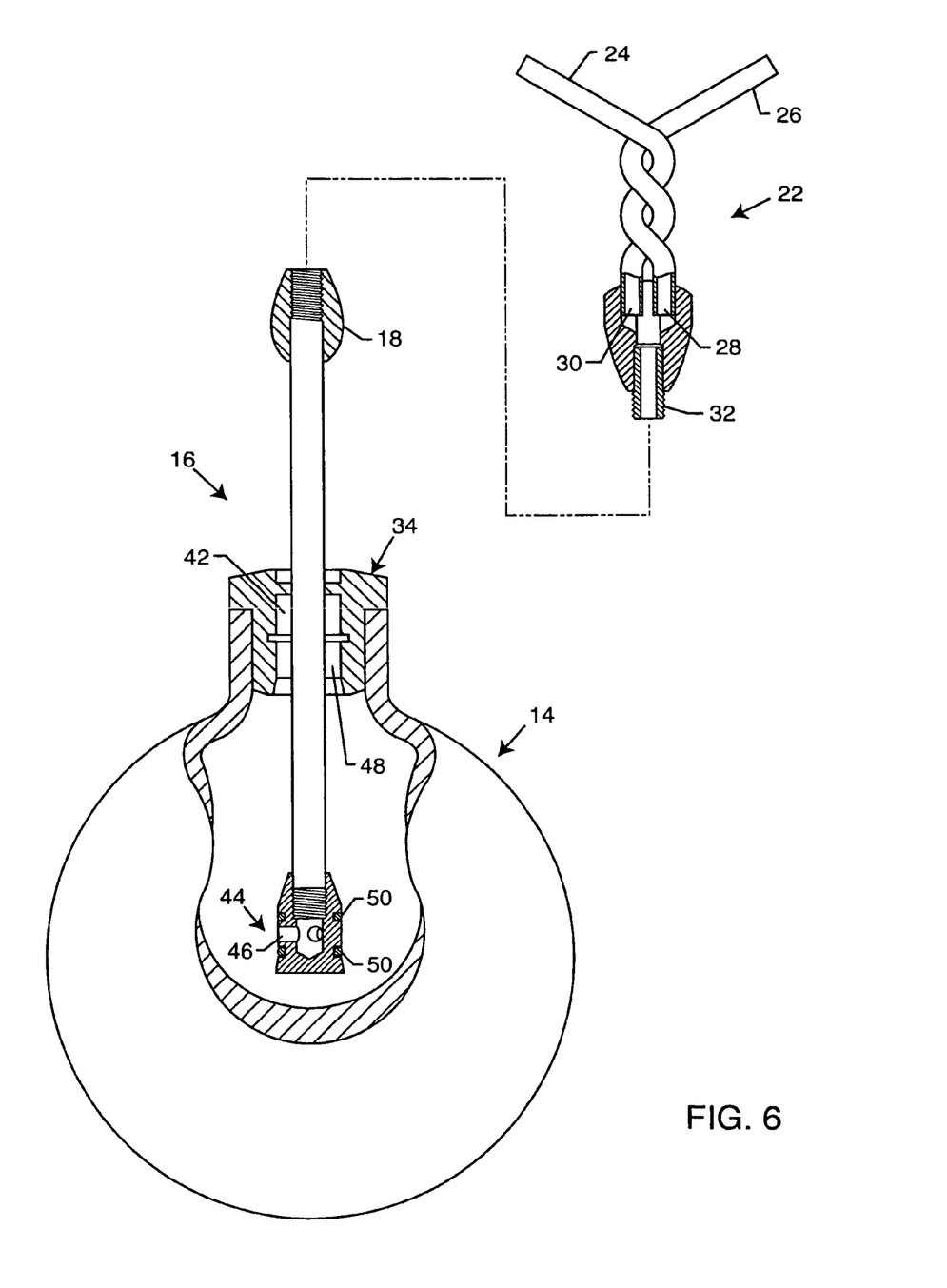
FIG. 6 is a partially sectioned elevational view, illustrating various component parts of the device of the present invention, illustrating the blow-pipe inserted into the vessel.

With particular reference to FIGS. 4 and 5, there are instances when two or more individuals' breath are desirably retained within the vessel 14. In such instance, the blow-pipe 16 is modified so as to have multiple inlets such that multiple individuals can breath simultaneously into the vessel 14. In a particularly preferred embodiment, as illustrated, a blow-pipe adaptor 22 is provided which is removably attachable to the mouthpiece 18 of the blow-pipe 16, such as by a threaded attachment, press-fit attachment, or any other suitable attachment means. As illustrated in FIGS. 4-6, a blow-pipe adapter 22 includes two hollow tubes 24 and 26 whose free ends thereof serve as inlets such that each individual can press his or her lips over the respective tube 24 and 26 and blow therein to fill the vessel 14 with their collective breath. Such may be desirable with lovers, newlyweds, etc., which could express their love for one another and capture their collective breath within the vessel 14.

With particular reference to FIG. 6, it will be seen that each hollow pipe 24 and 26 has an outlet 28 and 30, respectively, in fluid communication with an outlet pipe 32 of the adaptor 22, which is insertable into the mouthpiece 18 or hollow tube of the blow-pipe 16, such that the multiple individuals' breath are transferred to the hollow blow-pipe 16 and into the vessel 14.

With particular reference to FIG. 5, in a particularly preferred embodiment, as described above, the vessel 14 is comprised of a glass bulb having an opening 20. In such an embodiment, a neck 34 is preferably disposed within this opening 20. As such, the neck 34 includes a hollow shaft 36 which extends into the vessel 14 and a collar 38 which extends over the lip 40 of the opening 20 upper vessel 14. The neck 34 can be integrally formed with the vessel 14 as it is manufactured, or attached to the vessel 14 as a later step during the manufacturing process.

The neck 34 includes a passageway 40 extending therethrough, as illustrated in FIG. 6, through which the blow-pipe 16 is slidably inserted. Such slidable motion is illustrated in FIG. 5 by the phantom lines of the blow-pipe 16. Preferably, the passageway 40 is of slightly larger diameter than the hollow blow-pipe 16, such that as the individual's breath is introduced through the blow-pipe 16, at least a portion of the existing air within the vessel 14 is exhausted from the vessel 14 through the passageway 42.

With reference now to FIGS. 5 and 6, a plug 44, in the illustrated preferred embodiment, is removably attached to an end of the hollow blow-pipe 16, generally opposite the mouthpiece 18 so as to be disposed within the vessel 14. The plug 44 has a passageway 46 that extends from the hollow tube 16 and typically out a side wall of the plug 44. In this manner, the individual's breath passes through the mouthpiece 18, hollow pipe 16, and through the plug passageway 46 and into the vessel 14. The plug 44 has an outer surface conformation which engages and substantially mates with an inner chamber 48 of the neck 34. The plug 44 also preferably includes sealing means, such as O-rings 50, comprised of elastomeric material or the like which engage the inner walls of the chamber 48 so as to provide an air-tight seal therebetween. The plug 44 itself can be comprised of an elastomeric material which compresses slightly when received in the chamber 48 so as to form an air-tight seal without the need for O-rings and the like.

Figures 7, 8:
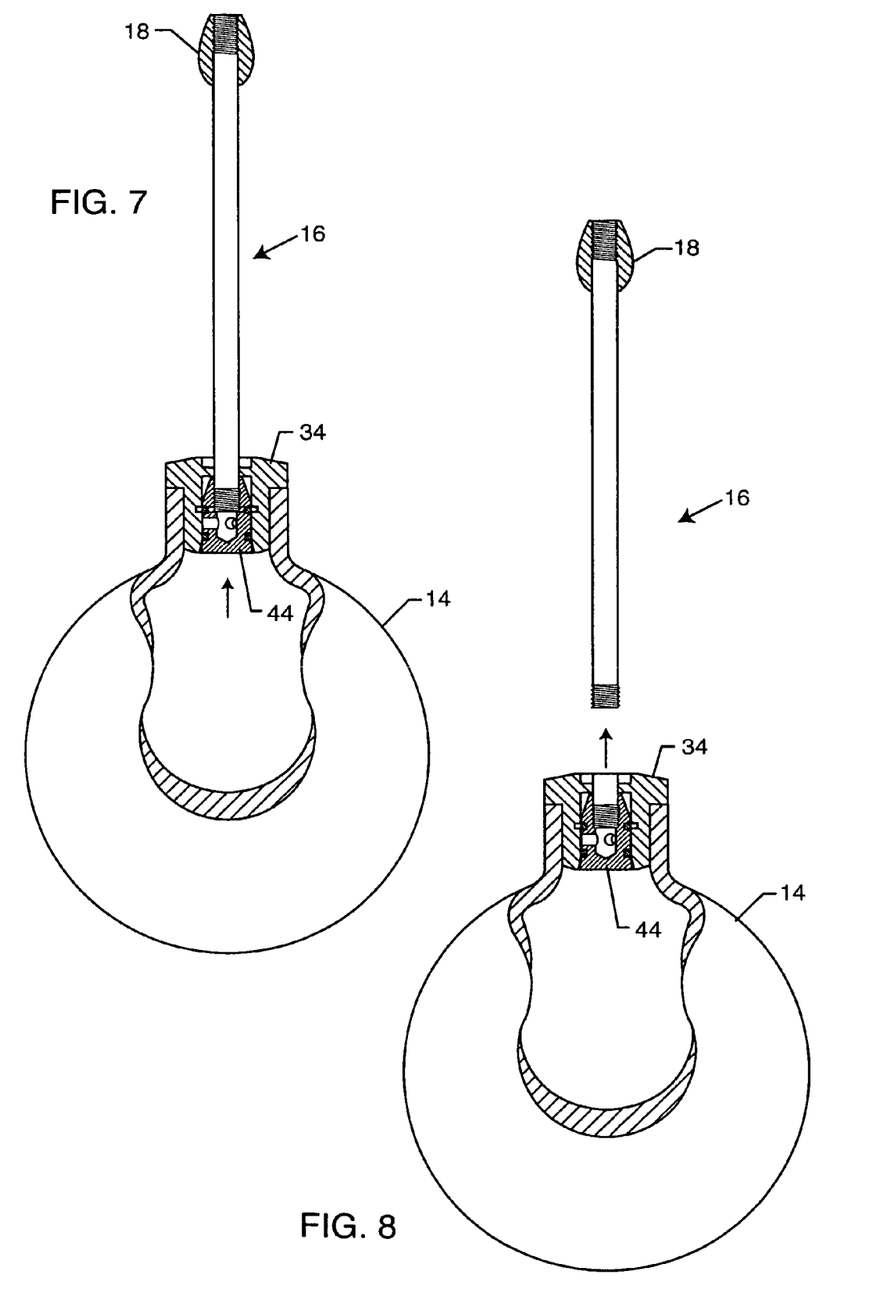
FIG. 7 is a partially sectioned elevational view of the vessel, with the blow-pipe extended outwardly such that a plug at the end thereof seals the aperture of the vessel.
FIG. 8 is a partially sectioned elevational view similar to FIG. 7, illustrating removal of the blow-pipe from the plug.

With reference now to FIGS. 6-8, with the plug 44 disposed within the vessel 14, the individual(s) blow into the vessel 14, through the blow-pipe 16 or adapter 22 to introduce their breath into the vessel 14. After doing so, the blow-pipe 16 is lifted outwardly from the vessel 14, causing the plug 44 to become lodged within the chamber 48 of the neck 34. Such action effectively seals off passageway 46, and thus the vessel 14. The plug 44 is removably attached to the blow-pipe 16, such that the blow-pipe 16 can be removed therefrom by pulling the blow-pipe 16 away from the plug 44, or more typically turning the blow-pipe 16 so as to unthread the connection between the blow-pipe 16 and the plug 44. With the plug 44 moved into a compressed position within the chamber of 48 of the neck 34, one or more individual's breath are entrapped within the vessel 14.

Figure 9:
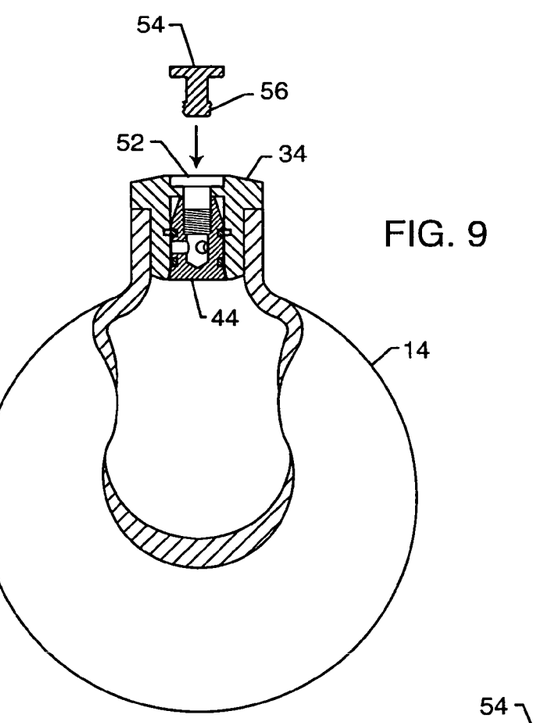
FIG. 9 is a sectional view similar to FIG. 8, illustrating a cap being inserted into a neck of the device.
Figure 10:
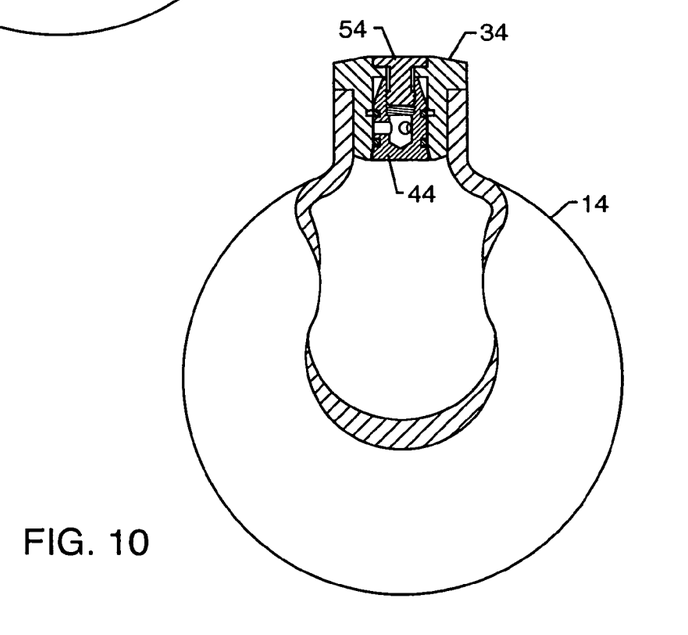
FIG. 10 is a partially sectioned elevational view of the device of the present invention sealed using the plug and cap.

With reference now to FIGS. 9 and 10, the plug 44 is susceptible to being pushed back into the vessel 14. Thus, the neck 34 includes a recess 52 into which a cap 54 fits. The cap 54 prevents the inadvertent or even intentional dislodgment of the plug 44. Preferably, the cap 54 rests within the recess 52 such that it is difficult to remove the cap 54. In a particularly preferred embodiment, the cap 54 external locking threads 56 which threadedly engage the internal threads of the plug 44, creating a permanent attachment. In this manner, the plug 54 cannot be removed and the individual's breath is captured permanently within the vessel 14.

Figures 11, 12:
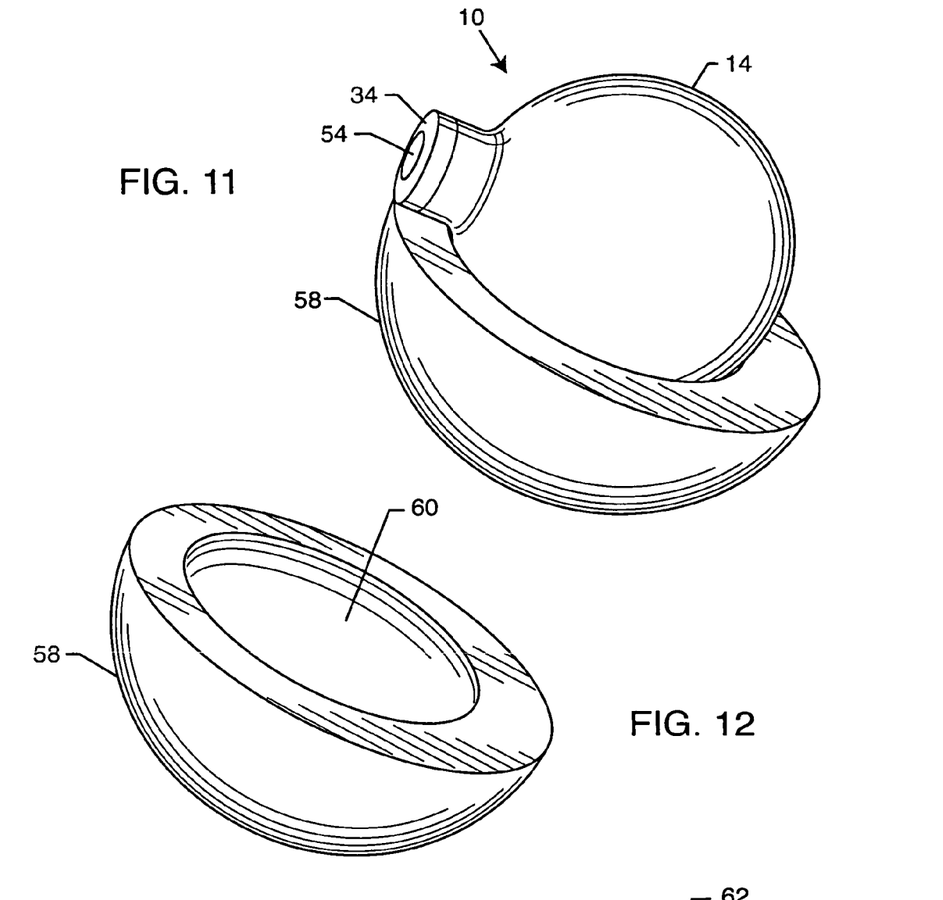
FIG. 11 a vessel, in the form a glass bowl, resting on a base, in accordance with the present invention.
FIG. 12 is a side perspective view of a base configured to hold the vessel, in accordance with the present invention.
Figure 13:
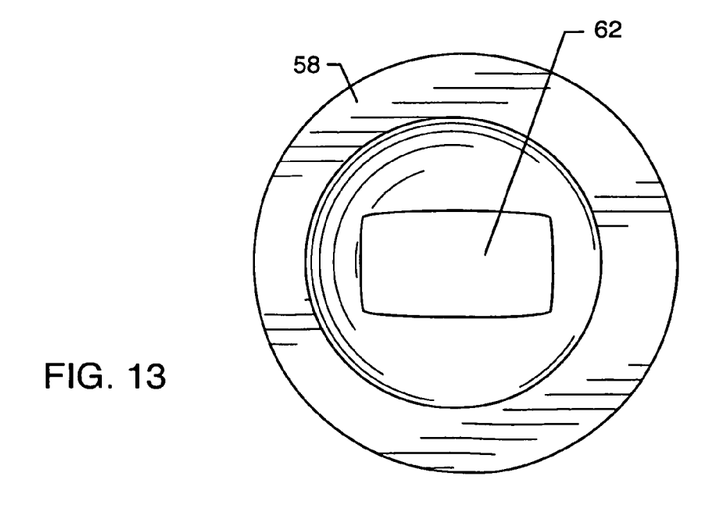
FIG. 13 is a top plan view of the base, illustrating a slot for retaining a photograph or written material therein, in accordance with the present invention.

With reference now to FIGS. 11-13, after sealing the vessel 14, as described above, the vessel 14 is preferably stored on a base 58. The base 58 is preferably ornate in design so as to be suitable for display in one's home or the like. The base 58 also securely holds the vessel 14. The base 58 may also be comprised of a glass material, although it is not limited to such. The base 58 preferably includes a cradle portion 60 which is configured so as to receive the glass bulb vessel 14. In a particularly preferred embodiment, the base 58 includes a slot or window 62 into which can be placed a photograph of the individual whose breath is contained within the vessel 14, or the couple or multiple individuals whose combined breath is contained within the vessel 14. Alternatively, the window or slots 62 can hold written material, such as a poem, handwritten note from the loved one, etc.

The device 10 of the present invention is particularly designed for use in capturing the essence or memory of an individual by retaining his or her breath which is a part of the individual while he or she is living. It will be appreciated that the device 10 invention can be used in a "ring" ceremony or the like for the newlyweds or couples expressing their love for one another. For example, after being married in the church, the bride and groom can meet alone or with a small group of friends and family and perform a ceremony wherein their breath is commingled and captured within the vessel 14, such as by using the blow-pipe adaptor 22 as described above. Statements or poems can be read at that time to memorialize the event and give it additional meaning. Alternatively, an individual can perform a similar ceremony alone with his or her loved one by reciting a poem or the like and inserting his or her breath alone into the vessel 14 for a keepsake to the other individual.

Although several embodiments have been described in detail for purposes of illustration, various modifications may be made to each without departing from the scope and spirit of the invention. Accordingly, the invention is not to be limited, except as by the appended claims.

What is claimed is:

1. A method for permanently capturing an individual's breath as a keepsake, comprising the steps of:
   providing a vessel capable of entrapping an individual's breath, the vessel including an air inlet aperture having a hollow blow pipe slidably inserted therein, the hollow blow pipe having a plug threadedly attached to an end thereof disposed within the vessel, the plug being adapted to seal the air inlet aperture;
   the individual blowing through the hollow blow pipe and into the vessel to expel air within the vessel while introducing the individual's breath into the vessel; and
   sealing the vessel to permanently trap the individual's breath therein by pulling the hollow blow pipe out of the aperture until the plug at the end thereof engages and seals the aperture, and unscrewing the hollow blow pipe from the plug.

2. The method of claim 1, wherein the vessel comprises a glass bulb.

3. The method of claim 1, wherein the blow pipe has a mouth piece at an end thereof.

4. The method of claim 1, wherein the vessel aperture is defined by a neck configured to receive the plug therein to seal the vessel.

5. The method of claim 4, wherein the neck is configured to receive a cap therein.

6. The method of claim 1, including the step of providing a blow pipe extending through the aperture and having multiple inlets to introduce the breath of two or more individual's simultaneously.

7. The method of claim 1, including the step of providing a base and displaying the vessel on the base.

8. The method of claim 7, including the step of displaying a photograph or writing with the base.

9. The method of claim 1, including the step of reciting a poem before the breathing step.

10. The method of claim 1, wherein the method of claim 1 is conducted as part of wedding ceremony.

11. The method of claim 1, wherein the method of claim 1 is conducted to express the individual's love for another.

12. The method for conducting a ceremony, comprised in the steps of:
    providing a vessel capable of entrapping an individual's breath;
    reading a previously prepared statement;
    breathing into an aperture of the vessel to introduce one or more individuals' breath within the vessel;
    sealing the vessel to entrap the one or more individuals' breath therein; and
    displaying the vessel on a base having a photograph or writing pertaining to the ceremony associated therewith.

13. The method of claim 12, wherein the breathing steps comprise of a step of inserting a hollow blow pipe having one or more mouthpieces at an end thereof into an aperture of the vessel.

14. The method of claim 13, wherein the sealing step includes the step of removing the blow pipe from the vessel after introducing the one or more individuals' breath therein, while moving a plug at the end of the blow pipe into the vessel's aperture.

15. The method of claim 5, including the step of threading an end of the cap into the plug sealing the aperture.

16. The method of claim 1, wherein the vessel includes only a single air inlet aperture.

17. A method for permanently capturing an individual's breath as a keepsake during a ceremony to express the individual's love for another, comprising the steps of:
    providing a vessel capable of entrapping an individual's breath, the vessel comprising a glass bulb having a single neck defining an air inlet aperture having a hollow blow pipe slidably inserted therein, the hollow blow pipe having a plug threadedly attached to an end thereof disposed within the vessel, the plug being adapted to seal the air inlet aperture;
    the individual blowing through the hollow blow pipe and into breathing into an aperture of the vessel to expel air within the vessel while introducing the individual's breath into the vessel;
    sealing the vessel to permanently trap the individual's breath therein by pulling the hollow blow pipe out of the aperture until the plug at the end thereof engages and seals the aperture, and unscrewing the hollow blow pipe from the plug; and
    inserting a cap into the neck and threadedly attaching the cap to the plug.

18. The method of claim 17, wherein the blow pipe has a mouth piece at an end thereof.

19. The method of claim 17, including the step of providing a blow pipe extending through the aperture and having multiple inlets to introduce the breath of two or more individual's simultaneously.

20. The method of claim 17, including the step of providing a base and displaying the vessel on the base.

21. The method of claim 20, including the step of displaying a photograph or writing with the base.

22. The method of claim 17, including the step of reciting a poem before the breathing step.

* * * * *